United States Patent [19]

Uchida et al.

[11] Patent Number: 5,118,811
[45] Date of Patent: Jun. 2, 1992

[54] NOVEL AMINO ACID DERIVATIVES POSSESSING PROLYL ENDOPEPTIDASE-INHIBITORY ACTIVITIES

[75] Inventors: Itsuo Uchida; Koji Kobayashi; Kazuhiko Nishii, all of Yokohama; Kunio Iwata; Shin Hara, both of Hatano; Koretake Anami, Nakatsu, all of Japan

[73] Assignees: Japan Tobacco Inc., Tokyo; Yoshitomi Pharmaceutical Industries, Ltd., Osaka, both of Japan

[21] Appl. No.: 613,737

[22] PCT Filed: Apr. 11, 1990

[86] PCT No.: PCT/JP90/00489
§ 371 Date: Dec. 12, 1990
§ 102(e) Date: Dec. 12, 1990

[87] PCT Pub. No.: WO90/12005
PCT Pub. Date: Oct. 18, 1990

[30] Foreign Application Priority Data

Apr. 13, 1989 [JP] Japan .................................. 1-91795

[51] Int. Cl.$^5$ .................. C07D 403/02; C07D 403/14; C07D 417/02; C07D 417/14
[52] U.S. Cl. .................................... 548/200; 530/330; 530/331; 548/201; 548/518; 548/533; 548/540
[58] Field of Search .............. 548/200, 201, 540, 533, 548/518; 514/17, 18; 530/330, 331

[56] References Cited

U.S. PATENT DOCUMENTS

| | | | |
|---|---|---|---|
| 4,162,325 | 7/1979 | Rodriguez | 548/550 |
| 4,687,778 | 8/1987 | Tanaka et al. | 514/419 |
| 4,701,465 | 10/1987 | Tanaka et al. | 514/423 |
| 4,743,616 | 5/1988 | Tanaka et al. | 514/423 |
| 4,857,514 | 8/1989 | Furukawa et al. | 514/227.5 |
| 4,857,537 | 8/1989 | Tode | 514/365 |
| 4,873,342 | 10/1989 | Tanaka et al. | 548/518 |
| 4,956,380 | 9/1990 | Toda et al. | 514/422 |
| 4,977,180 | 12/1990 | Tode | 514/365 |
| 4,983,624 | 1/1991 | Tode | 514/365 |

FOREIGN PATENT DOCUMENTS

115973 8/1984 European Pat. Off. ............ 548/540

(List continued on next page.)

OTHER PUBLICATIONS

Tsuru et al., J. Biochem. 104, pp. 580-586 (1988).

*Primary Examiner*—Robert Gerstl
*Attorney, Agent, or Firm*—Wenderoth, Lind & Ponack

[57] ABSTRACT

Amino acid derivatives of the formula

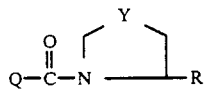

(I)

wherein:
Q is W—(CH$_2$)$_m$—(A)$_n$—CO—B— wherein
A is oxygen atom or —NH—;
B is

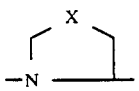

or —(CH$_2$)$_l$— wherein X is sulfur atom or —CH$_2$—, and l is an integer from 1 to 3;
W is

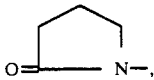

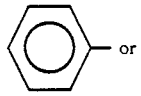

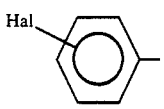

wherein Hal is halogen atom;
n is an integer of 0 or 1; and
m is an integer from 0 to 3;
Y is sulfur atom or —CH$_2$—; and
R is hydrogen atom, formyl group, C$_{1-5}$ alkoxycarbonyl group, —C≡N or $$-C=N-R^2$$
$$\phantom{-C=}|$$
$$\phantom{-C=N-}R^1$$

wherein
R$^1$ is hydrogen atom, and
R$^2$ is hydroxyl group, C$_{1-5}$ alkylcarboxy group, phenylcarboxy group, C$_{1-5}$ alkoxy group or phenyl C$_{1-5}$ alkoxy group;
with the proviso that when R is hydrogen atom, formyl group or C$_{1-5}$ alkoxycarbonyl group, W is

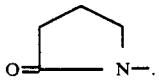

The compounds mentioned above specifically inhibit prolyl endopeptidase activity and are useful as agents for the treatment and prevention of dementia and amnesia.

1 Claim, No Drawings

FOREIGN PATENT DOCUMENTS

| | | |
|---|---|---|
| 0172458 | 2/1986 | European Pat. Off. . |
| 0201741 | 11/1986 | European Pat. Off. . |
| 0268190 | 5/1988 | European Pat. Off. . |
| 0268281 | 5/1988 | European Pat. Off. . |
| 0280956 | 9/1988 | European Pat. Off. . |
| 0303434 | 2/1989 | European Pat. Off. . |
| 0321956 | 6/1989 | European Pat. Off. . |
| 0322765 | 7/1989 | European Pat. Off. . |
| 384341 | 8/1990 | European Pat. Off. ............ 548/540 |
| 0414903 | 3/1991 | European Pat. Off. . |
| 3300316 | 7/1984 | Fed. Rep. of Germany ...... 548/540 |
| 1-156957 | 6/1989 | Japan . |
| 1-230578 | 9/1989 | Japan . |

NOVEL AMINO ACID DERIVATIVES POSSESSING PROLYL ENDOPEPTIDASE-INHIBITORY ACTIVITIES

FIELD OF ART

The present invention relates to novel amino acid derivatives possessing prolyl endopeptidase-inhibitory activities, represented by the formula (I)

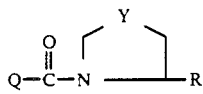

wherein:
Q is W—$(CH_2)_m$—$(A)_n$—CO—B— wherein
A is oxygen atom or —NH—;
B is

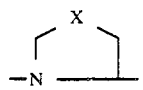

or —$(CH_2)_l$— wherein X is sulfur atom or —$CH_2$—, and l is an integer from 1 to 3;
W is

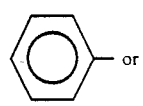

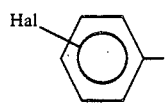

· wherein Hal is halogen atom;
n is an integer of 0 or 1; and
m is an integer from 0 to 3;
Y is sulfur atom or —$CH_2$—; and
R is hydrogen atom, formyl group, $C_{1-5}$ alkoxycarbonyl group, —C≡N or

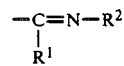

wherein
$R^1$ is hydrogen atom, and
$R^2$ is hydroxyl group, $C_{1-5}$ alkylcarboxy group, phenylcarboxy group, $C_{1-5}$ alkoxy group or phenyl $C_{1-5}$ alkoxy group;
with the proviso that when R is hydrogen atom, formyl group or $C_{1-5}$ alkoxycarbonyl group, W is

The novel amino acid derivatives of the present invention are useful as agents for the treatment and prevention of dementia and amnesia.

BACKGROUND ART

Along with the arrival of an aging society, the medical treatment for the senile has been drawing much attention. Above all, senile dementia has become a serious social problem, and various developments have been made in an attempt to provide new pharmaceuticals to cope with the problem. However, while the agents for the treatment of amnesia and dementia are effective for the improvement of peripheral symptoms such as depression, emotional disturbances, abnormal behavior, etc., they do not show definite effects on the central symptoms of dementia, such as memory disorder, disorientation, or the like. Thus, the development of medicaments which can offer dependable action and effect on these symptoms is earnestly desired.

In the meantime, prolyl endopeptidase; EC, 3.4.21.26 is known to act on peptides containing proline and specifically cleaves out the carboxyl side of the proline. Further, this enzyme is known to act on hormones and neurotransmitters such as TRH (thyrotropin-releasing hormone), substance P, neurotensin, etc. as well as on vasopressin which is supposedly concerned with learning and memory process, resulting in decomposition and inactivation of them.

In view of the foregoing, a compound possessing inhibitory activity on prolyl endopeptidase is expected to suppress decomposition and inactivation of vasopressin, etc., thereby suggesting a potential application thereof to the treatment and prevention of amnesia and demntia as an efficacious medicament which exhibits direct action on the central symptoms of dementia [See Seikagaku, 55, 831 (1983); FOLIA PHARMACOL. JAPON, 89, 243 (1987); and J. Pharmacobio-Dyn., 10, 730 (1987)] and also to suppress decomposition and inactivation of hormones and neurotransmitters such as TRH, substance P, neurotensin, etc., thereby improving various symptoms caused by the decomposition and inactivation of these substances.

Based on the motivation described above, there have been attempted to develop prolyl endopeptidase-inhibiting agents and the following derivatives are known:

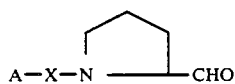

(1)

wherein A is amino-protective group and X is amino acid residue, U.S. Pat. No. 4,687,778;

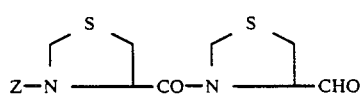

(2)

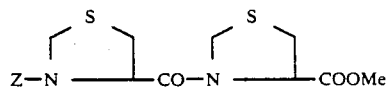

wherein Z is benzyloxycarbonyl group, EP 322765, U.S. Pat. No. 4,857,524;

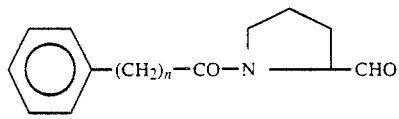 (3)

wherein n is an integer from 1 to 4, U.S. Pat. No. 4,743,616;

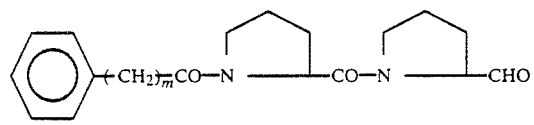 (4)

wherein m is an integer from 1 to 8, U.S. Pat. No. 4,873,342;

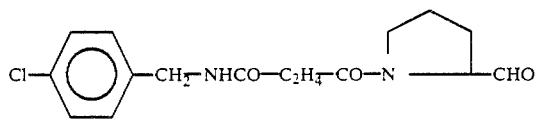 (5)

EP 268190; and

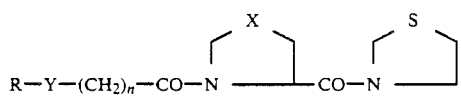 (6)

wherein R is alkyl group or phenyl group which may be substituted, Y is —O—, —CO— or —CH$_2$—, n is an integer of 2 or 3 and X is —S—, —CH$_2$— or —CH(OH)—, Japanese Patent Unexamined Publication No. 301671/1989.

However, a compound wherein nitrile group or oxime group has been introduced to the site corresponding to the carboxyl terminal or 2-oxopyrrolidinyl group has been introduced to the site corresponding to the amino terminal as in the compounds of the present invention represented by the formula (I) has not been within the public knowledge.

DISCLOSURE OF THE INVENTION

Based on the findings mentioned above, the present inventors have conducted intensive studies to find a compound which possesses an amino acid as a fragment, specifically inhibits the prolyl endopeptidase activity and acts as an antiamnesia agent which directly acts on the central symptoms of amnesia and dementia.

As a result, it has been found that the novel amino acid derivatives of the following formula (I) possess specific and remarkable prolyl endopeptidase-inhibitory activities.

According to the present invention, the novel amino acid derivatives are represented by the following formula (I)

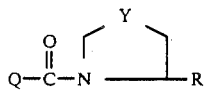 (I)

wherein:
Q is W—(CH$_2$)$_m$—(A)$_n$—CO—B— wherein

A is oxygen atom or —NH—;
B is

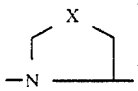

or —(CH$_2$)$_l$— wherein X is sulfur atom or —CH$_2$—, and l is an integer from 1 to 3;
W is

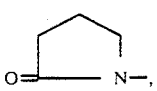,

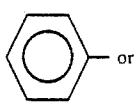 or

wherein Hal is halogen atom;
n is an integer of 0 or 1; and
m is an integer from 0 to 3;
Y is sulfur atom or —CH$_2$—; and
R is hydrogen atom, formyl group, C$_{1-5}$ alkoxycarbonyl group, —C≡N or $$-\underset{R^1}{\underset{|}{C}}=N-R^2$$

wherein
R$^1$ is hydrogen atom, and
R$^2$ is hydroxyl group, C$_{1-5}$ alkylcarboxy group, phenylcarboxy group, C$_{1-5}$ alkoxy group or phenyl C$_{1-5}$ alkoxy group;
with the proviso that when R is hydrogen atom, formyl group or C$_{1-5}$ alkoxycarbonyl group, W is

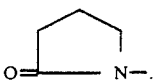.

In the above definition,

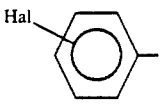

is phenyl group substituted by halogen atom such as Cl, Br and F, and is preferably 4-chlorophenyl. The C$_{1-5}$ alkyl in the C$_{1-5}$ alkoxycarbonyl group, C$_{1-5}$ alkylcarboxy group and C$_{1-5}$ alkoxy group is straight or branched hydrocarbon having 1 to 5 carbon atom(s), and is exemplified by methyl, ethyl, propyl, butyl, isopropyl, sec-butyl, tert-butyl, pentyl, isopentyl, and so on.

Hereunder follows the description of the methods for producing the novel amino acid derivatives (I) of the present invention.
There are various methods for the production of the novel amino acid derivatives (I) of the present invention, and one example of the reaction sequence is given below.
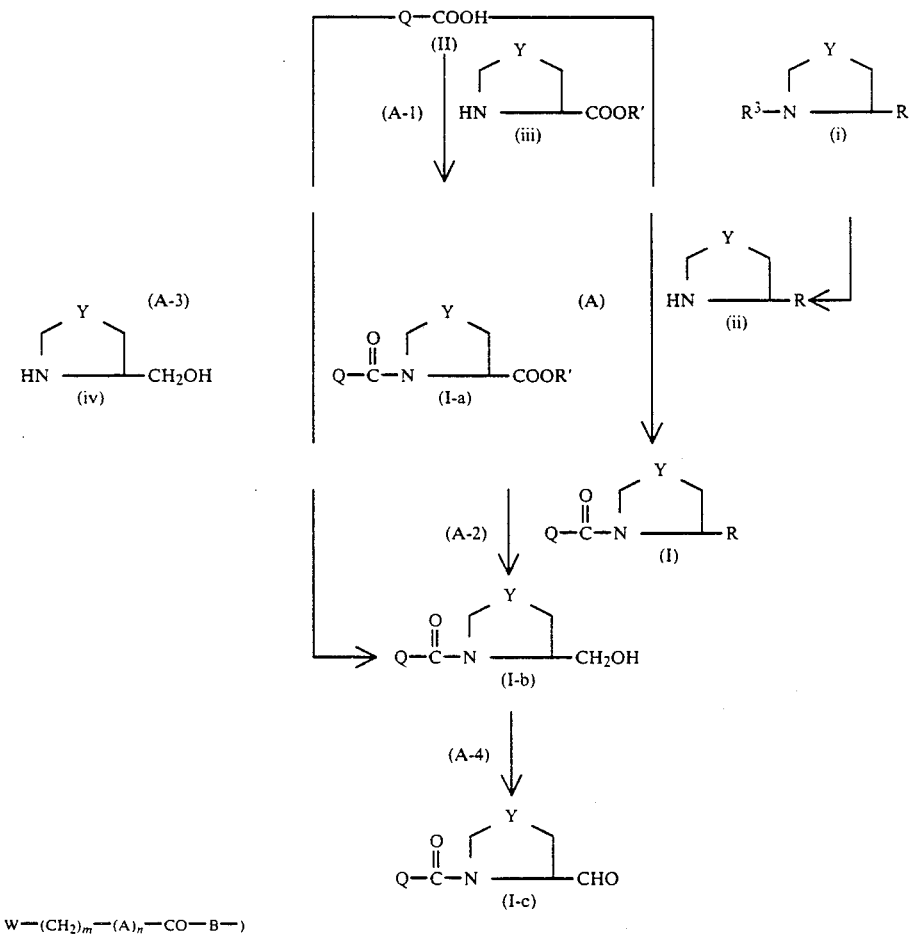
(Q is W—(CH$_2$)$_m$—(A)$_n$—CO—B—)
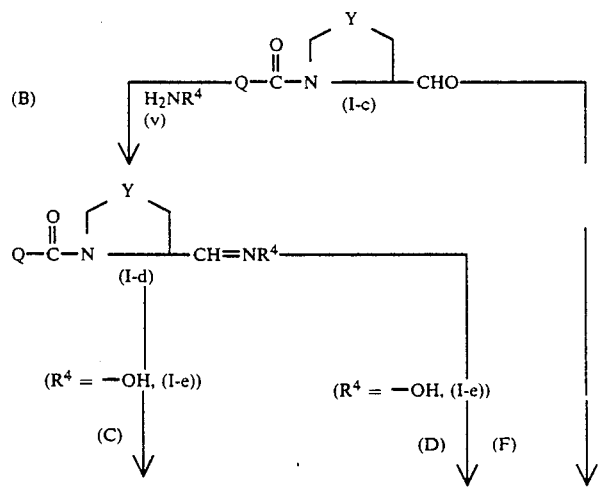

Flow 2
Production (2) of the compound (I)

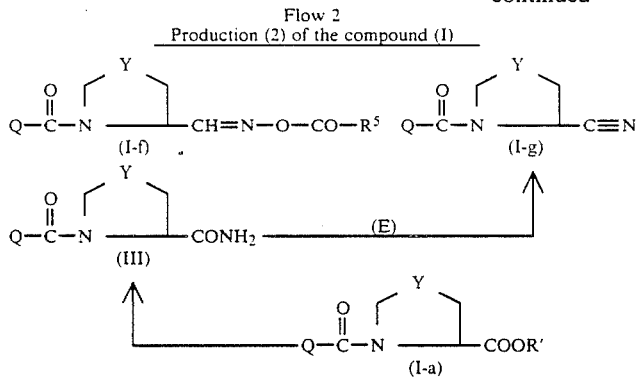

Each of the above-mentioned processes is discussed in the following. The symbols Q, W, R, $R^1$, $R^2$, A, B, X, Y, l, m, n, etc. are as defined above.

REACTION (A)

The object compound (I) is obtained by eliminating the amino-protective group $R^3$ from an intermediate compound of the formula (i) by a known method to give an imino compound (ii), which is then subjected to condensation reaction with a compound of the formula (II).

This condensation reaction per se is the one normally employed for conventional peptide syntheses, and any other known method can be employed for Reaction (A).

The elimination reaction of the amino-protective group $R^3$ differs depending on the kind of the protective group to be involved. For example, when $R^3$ is benzyloxycarbonyl group (Z), the elimination is conducted by hydrogenation of the intermediate compound of the formula (i), or by treatment with an acid such as hydrobromic acid-acetic acid, trifluoromethanesulfonic acid, etc.; and when $R^3$ is tert-butoxycarbonyl group (Boc), benzhydryl group, trityl group, etc., the elimination is conducted by acid treatment of the intermediate compound of the formula (i) with hydrobromic acid, hydrochloric acid, formic acid, trifluoroacetic acid, or the like.

The reaction is preferably conducted in a suitable solvent such as water, methanol, ethanol, acetic acid, dioxane, etc. or without solvent at a temperature between $-30°$ C. and $70°$ C., preferably between $0°$ C. and $30°$ C.

Thereafter, the amino acid derivatives (I) can be obtained by condensation reaction of the imino compound (ii) thus obtained and the compound (II) by a conventional method.

A method known per se can be employed for this peptide formation. Examples thereof include methods using dicyclohexylcarbodiimide (DCC) as a condensing agent, activation ester methods, mixed acid anhydride method, azide methods, acid chloride methods, and so on. The reaction proceeds in an inert solvent at a temperature between $0°$ C. and under heating. Examples of suitable solvents include chloroform, diethyl ether, dimethylformamide, ethyl acetate, dichloromethane, tetrahydrofuran, or the like.

In the activation ester method, peptide bonds are formed by reacting the above-mentioned compound (II) with p-nitrophenol, thiophenol, p-nitrothiophenol, N-hydroxysuccinimide, etc. in an inert solvent in the presence of DCC, thereby affording an active ester (e.g. an ester with N-hydroxysuccinimide), and with or without isolation, further reacting the same with the above-mentioned imino compound (ii) in an inert solvent at a temperature between $0°$ C. and $40°$ C.

In the mixed acid anhydride method, peptide bonds are formed by reacting the above-mentioned compound (II) with an acid halide (e.g. pivaloyl chloride, tosyl chloride, oxalyl chloride) or an acid derivative (e.g. ethyl chloroformate, isobutyl chloroformate) in an inert solvent in the presence of a tertiary amine (e.g. pyridine, triethylamine) at a temperature between $0°$ C. and $40°$ C., thereby affording a mixed acid anhydride, and further reacting the same with the imino compound (ii) mentioned above at a temperature between $0°$ C. and $40°$ C.

In the DCC method, the desired peptide bonds are formed by reacting the above-mentioned compounds (ii) and (II) in an inert solvent in the presence or absence of the tertiary amine mentioned above such as triethylamine, or with or without addition of a suitable additive [e.g. 1-hydroxybenzotriazole (HOBt), N-hydroxy-5-norbornen-2,3-dicarboximide (HONB)] with DCC as a condensing agent.

The intermediates of formulas (i) and (ii) are commercially available, or known per se, or easily prepared by the following method.

That is, the intermediate (i) having a desired substituent R (e.g. $-CH=NOH$, $-C\equiv N$) can be obtained by using as a starting material the following compounds known before the present application:

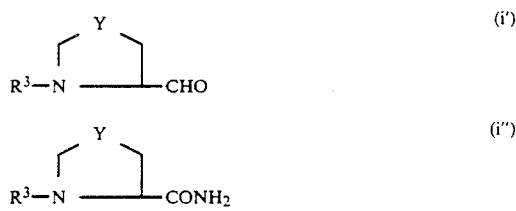

wherein Y is as defined above and $R^3$ is protective group, by a method similar to Reaction (B), (C), (D), (E) or (F) to be mentioned later. For example, the intermediate (i) wherein R is $-CH=NOH$ can be obtained by reacting a compound (i') above as a starting material with $H_2NOH$ according to Reaction (B).

REACTION (A-1)

The compound (I-a), one of the final compounds of the present invention, is obtained by subjecting a compound of the formula (II) to condensation reaction with proline $C_{1-5}$ alkyl ester or thioproline $C_{1-5}$ alkyl ester of the formula (iii) wherein R is $C_{1-5}$ alkyl group.

As mentioned above under Reaction (A), any method known as a peptide forming reaction in peptide syntheses can be employed for this condensation reaction.

REACTION (A-2)

A compound of the formula (I-a) is reduced with the use of lithium borohydride, sodium borohydride, etc. to give an alcohol compound of the formula (I-b). This reduction can be carried out, for example, in an anhydrous inert solvent such as tetrahydrofuran, diglyme, dioxane, etc. with the use of lithium borohydride, or in a solvent such as methanol, ethanol, diglyme, etc. with the use of sodium borohydride, at a temperature between $-10°$ C. and reflux temperature, preferably between 0° C. and room temperature.

REACTION (A-3)

A compound of the formula (II) is subjected to condensation reaction with prolinol or thioprolinol of the formula (iv) to give the compound (I-b).

Any method known as a peptide formation can be used for this condensation reaction, as discussed in Reaction (A) above.

REACTION (A-4)

The alcohol compound of the formula (I-b) as obtained in Reaction (A-2) or (A-3) mentioned above is oxidized with sulfur trioxide pyridine complex, pyridinium chlorochromate, pyridinium dichromate, etc. to give the compound (I-c), one of the object compounds of the present invention.

The oxidation from the compound (I-b) to the compound (I-c) proceeds in an anhydrous organic solvent such as dimethylsulfoxide, benzene, etc. in the presence of a tertiary amine such as triethylamine, using sulfur trioxide pyridine complex at a temperature between $-10°$C. and room temperature, preferably between 5° C. and 15° C., or in an anhydrous inert solvent such as methylene chloride, etc., using pyridinium chlorochromate or pyridinium dichromate at a temperature from 0° C. to reflux temperature, preferably from 0° C. to room temperature.

REACTION (B)

A compound of the formula (I-c) and a compound of the formula $$H_2NR^4 \qquad (V)$$

Wherein $R^4$ is hydroxyl group, $C_{1-5}$ alkoxy group, phenyl $C_{1-5}$ alkoxy group, or a salt thereof are subjected to condensation reaction to give the object compound (I-d).

That is, the condensation reaction is carried out by reacting the compounds (I-c) and (V) or salts thereof in a solvent such as water, dimethylformamide, methanol, ethanol, dioxane, tetrahydrofuran, etc. in the presence or absence of a base (e.g. sodium carbonate, potassium carbonate, sodium hydroxide, pyridine triethylamine) at a temperature between 0° C. and 100° C., preferably between room temperature and 70° C. Examples of the salts of the compound (V) include hydrochloride, sulfate, citrate, etc., with preference given to hydrochloride.

Phenyl $C_{1-5}$ alkoxylamine wherein $R^4$ is phenyl $C_{1-5}$ alkoxy can be prepared from the corresponding phenyl $C_{1-5}$ alkyl alcohol or phenyl $C_{1-5}$ alkyl halide by a known method, for example, the method described in Organic Functional Group Preparation 3, 321-364 (1972), Academic Press. The compound wherein $R^4$ is phenyloxy can be also prepared in the same manner, which shall be readily understood by those skilled in the art.

REACTION (C)

A compound of the formula (I-e) is reacted with a carboxylic acid, carboxylic acid anhydride or carboxylic acid halide of the formulas ① $R^5COOH$
② $(R^5CO)_2O$
③ $R^5COHal$ wherein $R^5$ is $C_{1-5}$ alkyl group or phenyl group, compound (I-f), one of the object compounds of the present invention. Either of ① to ③ mentioned above is reacted in an anhydrous inert solvent such as dimethylformamide, benzene, chloroform, methylene chloride, ether, or the like. Preferably, the following reaction conditions are employed, depending on the mode of the carboxylic acid to be employed.

① carboxylic acid

The reaction is carried out in the presence of an acid catalyst (e.g. sulfuric acid, hydrochloric acid, acetic acid, p-toluenesulfonic acid, etc.) at a temperature between 0° C. and reflux temperature.

② carboxylic acid anhydride

The reaction is carried out in the presence of a base (e.g. pyridine, triethylamine, N,N-dimethylaniline, alminium alcohlate, etc.) or an acid catalyst (e.g. sulfuric acid, hydrochloric acid, acetic acid, p-toluenesulfonic acid, etc.) at a temperature between 0° C. and reflux temperature.

③ carboxylic acid halide

The reaction is carried out in the presence of a base (e.g. pyridine, triethylamine, N,N-dimethylaniline, alminium alcohlate, etc.) at a temperature between 0° C. and reflux temperature. Halogen of the acid halide may be chlorine, bromine or iodine, with preference given to chlorine.

REACTION (D)

A compound of the formula (I-e) is dehydrated to give the compound of the formula (I-g), one of the object compounds of the present invention.

The dehydration is carried out without solvent or in an inert solvent such as benzene, chloroform, ether, ethyl acetate, tetrahydrofuran, etc. using formic acid, acetic acid, acetic anhydride, phosphorus pentaoxide, thionyl chloride, etc. at a temperature between room temperature and reflux temperature, or in the same solvent in the presence of a tertiary amine (e.g. pyridine, triethylamine, etc.) using phosphononitorilic chloride at a temperature between 0° C. and room temperature, or in the same solvent using N,N'-carbonyldiimidazole at a temperature between 0° C. and room temperature.

REACTION (E)

A compound of the formula (III) is dehydrated with phosphorus pentoxide, phosphorus oxychloride, phosphorus pentachloride or thionyl chloride without solvent or in an inert solvent mentioned above, or with p-toluenesulfonic acid in pyridine as a solvent to give the compound of the formula (I-g).

REACTION (F)

The compound of the formula (I-g), one of the compounds of the present invention, is produced from a compound of the formula (I-c), and a few examples of the production methods are given below.

① A compound of the formula (I-c) is reacted with O-2,4-dinitrophenylhydroxylamine in an inert solvent in the presence of a mineral acid (e.g. hydrochloric acid, sulfuric acid) in a catalyst amount at a temperature between 0° C. and reflux temperature, preferably at room temperature, and further reacted with a base (e.g. sodium hydroxide, potassium hydroxide, triethylamine, etc.) at reflux temperature.

② A compound of the formula (I-c) is reacted with hydroxylamine-O-sulfonate in water suspension at a temperature between room temperature and 70° C.

③ A compound of the formula (I-c) is reacted with hydroxylamine hydrochloride in formic acid at a temperature between room temperature and reflux temperature.

④ A compound of the formula (I-c) is reacted with hydroxylamine hydrochloride in an inert solvent such as dimethylformamide in the presence of a base (e.g. a tertiary amine such as pyridine, triethylamine, etc.) at a temperature between room temperature and reflux temperature, and dehydrated with selenium dioxide.

In the reaction (F) mentioned above, a compound (I-c) is used as a starting material and the object compound (I-g) is produced continuously without isolation of intermediate products. In following the above-mentioned production ③ or ④ in which an oxime-type intermediate compound (I-e) is produced during the process, the intermediate compound (I-e) may be isolated between the reactions and thereafter, subjected to a reaction such as (D) mentioned above.

The intermediate compounds of the formula (II) above are discussed in detail in the following. The intermediate compounds Q—COOH have the following structure:

$$W-(CH_2)_m-(A)_n-CO-B-COOH$$

wherein A, B, W, m and n are as defined above.

The intermediate compounds Q—COOH can be prepared, for example, as follows:

$$W+CH_2)_{\overline{m}}(NH)_{\overline{n}}H + HOOC+CH_2)_{\overline{l}}COOMe \longrightarrow \quad ①$$

$$W+CH_2)_{\overline{m}}(NH)_{\overline{n}}CO+CH_2)_{\overline{l}}COOMe \longrightarrow$$

$$W+CH_2)_{\overline{m}}(NH)_{\overline{n}}CO+CH_2)_{\overline{l}}COOH$$

$$W+CH_2)_{\overline{m}}(O)_{\overline{l}}CO-Hal + H-N\underset{\phantom{X}}{\overset{X}{\frown}}COOMe \longrightarrow \quad ②$$

$$W+CH_2)_{\overline{m}}(O)_{\overline{l}}CO-N\underset{\phantom{X}}{\overset{X}{\frown}}COOMe \longrightarrow$$

$$W+CH_2)_{\overline{m}}(O)_{\overline{l}}CO-N\underset{\phantom{X}}{\overset{X}{\frown}}COOH$$

$$W+CH_2)_{\overline{m}}CO-OH + H-N\underset{\phantom{X}}{\overset{X}{\frown}}COOMe \longrightarrow \quad ③$$

$$W+CH_2)_{\overline{m}}CO-N\underset{\phantom{X}}{\overset{X}{\frown}}COOMe \longrightarrow$$

$$W+CH_2)_{\overline{m}}CO-N\underset{\phantom{X}}{\overset{X}{\frown}}COOH$$

In particular, the reaction ① is effective when n=1, A=—NH— or m=n=0 and W is $$O=\underset{\phantom{XX}}{\overset{\frown}{\phantom{X}}}N-;$$

the reaction ② is effective when n=1 and A=—O—; and the reaction ③ is effective when n=0.

Each reaction is detailedly discussed below. Reaction ①

An amine or amide of the formula: W—(CH$_2$)$_m$—(NH)$_n$—H and a carboxylic acid of the formula: HOOC—(CH$_2$)$_l$—COOMe are subjected to dehydrative condensation reaction, wherein a method known as a peptide bond formation can be employed, as described in Reaction (A) mentioned above. However, it is preferable that the following method be employed for the enhancement of the reactivity of N in the amide when m=n=0 and W=

$$O=\underset{\phantom{XX}}{\overset{\frown}{\phantom{X}}}N-.$$

That is, 2-oxopyrrolidine, an amide, is activated with n-butyllithium or sodium hydroxide in an anhydrous inert solvent such as tetrahydrofuran, diethyl ether, dioxane, etc. at a temperature between −70° C. and 0° C., preferably between −50° C. and −10° C., after which an acid anhydride or acid halide corresponding to the compound of the formula: HOOC—(CH$_2$)$_l$—COOMe is added thereto for reaction at a temperature between −70° C. and 0° C., preferably between −50° C. and 20° C. The thus-obtained compound of the formula: W—(CH$_2$)$_m$—(NH)$_n$—CO—(CH$_2$)$_l$—COOMe is hydrolyzed according to a known method in a solvent such as methanol, tetrahydrofuran, etc. with the use of a base such as sodium hydroxide, lithium hydroxide, etc. at a temperature between 0° C. and room temperature.

REACTION ②

An amino acid methyl ester of the formula:

$$HN\underset{\phantom{XX}}{\overset{X}{\frown}}COOMe$$

is reacted with a compound of the formula: $W-(CH_2)_m-(O)-CO-Hal$ water, etc. in the presence of a tertiary amine such as triethylamine, N-methylmorpholine, etc. or sodium hydroxide at a temperature between 0° C. and room temperature. The thus-obtained compound of the formula:

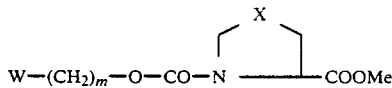

is hydrolyzed as in Reaction ① above.

REACTION ③

A carboxylic acid of the formula $W-(CH_2)_m-COOH$ and an amino acid methyl ester of the formula:

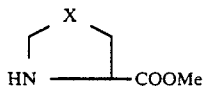

are subjected to condensation reaction, wherein a method known as a peptide bond formation can be employed, as discussed in detail in Reaction (A) mentioned above. Thereafter, the thus-obtained compound of the formula:

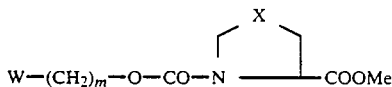

is hydrolyzed as in Reaction ① above.

The compounds of the formula (I) thus obtained can be purified from the reaction mixture by a conventional method selected ad libitum according to the purpose, which has been usually employed in the field of synthetic organic chemistry. For example, silica gel column chromatography, recrystallization, etc. can be used. The purification may be conducted at every reaction or upon completion of a few reactions.

A series of compounds mentioned above possess 1 or 2 asymmetric carbon(s) in each molecule. In the present invention, the configuration of each asymmetric carbon may be R, S or a mixture thereof. Optically active substances can be obtained respectively by employing optically active compounds as a starting material. Of the above-mentioned series of compounds, oxime compounds possess syn- or anti-geometric isomers. The present invention encompasses both of these isomers and a mixture thereof.

When the compounds of the present invention are used as a pharmaceutical, they are administered systemically or locally, orally or parenterally.

While the dose varies depending on age, weight, symptom, treatment effect, method of administration, etc., the compounds of the present invention can be administered orally at 1 mg to 500 mg per administration per adult in a single unit dosage or in divided doses daily, or parenterally (preferably, intravenously) at 1 mg to 100 mg per administration per adult once to several times daily.

The compounds of the present invention are used in the form of solid compositions and liquid compositions for oral administration, or injections, suppositories, etc. for parenteral administration.

The solid compositions for oral administration include tablets, pills, capsules, powders, granules, etc. In the solid compositions, at least one active substance is mixed with at least one inactive diluent, and excipients, binding agents, rublicants, degrading agents, dissolution enhancing agents, stabilizing agents, and so on may be also contained, if necessary. Tablets and pills may be applied with enteric coating, if necessary. Capsules include hard and soft capsules.

The liquid compositions for oral administration include solutions, emulsions, suspensions, syrups and elixirs. These liquid compositions contain inactive diluents generally used and may further contain adjuvants such as wetting agents and suspending agents, sweetners, flavors, aromatic agents and preservatives.

The injections for parenteral administration include sterile aqueous or non-aqueous solutions, suspensions and emulsions. At least one active substance is used with at least one inactive aqueous diluent or inactive non-aqueous diluent in admixture, and other adjuvants such as preservatives, wetting agents, emulsifiers, dispersibles, stabilizing agents and dissolution enhancing agents may be also contained. They are normally sterilized by filtration (bacteria-retaining filter, etc.), mixing with sterilizers or gamma irradiation, or they are, subsequent to such treatments, prepared into solid compositions by lyophilization and diluted before use with sterile water or sterile diluents for injection.

FORMULATION EXAMPLE 1

| Active substance | 10 parts |
|---|---|
| Lactose | 75 parts |
| Ground magnesium oxide | 15 parts |

The above ingredients were mixed homogeneously to give tablets and capsules.

FORMULATION EXAMPLE 2

| Active substance | 10 parts |
|---|---|
| Corn starch | 50 parts |
| Lactose | 40 parts |

The above ingredients were mixed homogeneously to give powders and granules.

FORMULATION EXAMPLE 3

| Active substance | 1 part |
|---|---|
| Surfactant | 5 parts |
| Physiological saline | 94 parts |

The above ingredients were mixed while heating and sterilized to give injections.

THE BEST MODE FOR THE EMBODIMENT OF THE INVENTION

The present invention is hereinbelow described in detail by way of examples.

The abbreviations used in the examples respectively mean the following:

| Z | benzyloxycarbonyl |
|---|---|

| | |
|---|---|
| DMF | dimethylformamide |
| DMSO | dimethylsulfoxide |
| THF | tetrahydrofuran |
| HOBt | 1-hydroxybenzotriazole |
| DCC | N,N'-dicyclohexylcarbodiimide |
| PLC | preparative thin layer chromatography |
| $^1$H NMR | proton nuclear magnetic resonance spectra |
| EI-MS | electron impulse ion mass spectra |

EXAMPLE 1

N-[(2-Oxo-1-pyrrolidinyl)acetyl]-L-prolyl-L-proline methyl ester (Compound 1)

A) N-[(2-Oxo-1-pyrrolidinyl)acetyl]-L-proline methyl ester

To a solution of L-proline methyl ester hydrochloride (8.28 g) in DMF (100 ml) were added N-methylmorpholine (5.50 ml), 2-oxo-1-pyrrolidine acetic acid (7.15 g) and HOBt (10.12 g) under ice-cooling. The mixture was cooled to −25° C., added with DCC (10.32 g), and stirred at room temperature for 16 hours. The precipitated dicyclohexylurea was filtered off, and the filtrate was concentrated. The residue was purified by silica gel column chromatography (chloroform-methanol) to give 12.94 g of N-[(2-oxo-1-pyrrolidinyl)acetyl]-L-proline methyl ester.

B) N-[(2-Oxo-1-pyrrolidinyl)acetyl]-L-proline

To a solution of N-[(2-oxo-1-pyrrolidinyl)acetyl]-L-proline methyl ester (5.06 g) in methanol (40 ml) was added dropwise a 2N sodium hydroxide solution (12 ml) under ice-cooling, and the mixture was stirred at room temperature for 3 hours. To the reaction mixture was added 3N hydrochloric acid under ice-cooling to adjust the mixture to pH 5. The reaction mixture was concentrated to dryness, suspended in chloroform and filtered. The filtrate was concentrated to give 4.28 g of N-[(2-oxo-1-pyrrolidinyl)acetyl]-L-proline.

C) N-[(2-Oxo-1-pyrrolidinyl)acetyl]-L-prolyl-L-proline methyl ester

To a solution of N-[(2-oxo-1-pyrrolidinyl)acetyl]-L-proline (3.01 g) in DMF (25 ml) were added L-proline methyl ester hydrochloride (2.07 g), HOBt (2.54 g) and N-methylmorpholine (1.38 ml). The mixture was cooled to −25° C., added with DCC (2.85 g), and stirred at a temperature of −25°-0° C. for 3 hours and at room temperature for 15 hours. The precipitated dicyclohexylurea was filtered off, and the filtrate was concentrated. The residue was purified by silica gel column chromatography (chloroform-methanol) to give 2.56 g of N-[(2-oxo-1-pyrrolidinyl)acetyl]-L-prolyl-L-proline methyl ester.

EXAMPLES 2 AND 3

In the same manner as in Example 1, the following Compounds 2 and 3 were obtained.

EXAMPLE 2

N-[(2-Oxo-1-pyrrolidinyl)acetyl]-L-prolyl-L-thioproline methyl ester (Compound 2)

The procedure of Example 1-C) was followed using L-thioproline methyl ester hydrochloride in place of L-proline methyl ester hydrochloride.

EXAMPLE 3

N-[(2-Oxo-1-pyrrolidinyl)acetyl]-L-thioprolyl-L-thioproline methyl ester (Compound 3)

The procedures of Examples 1-A) and 1-C) were followed using L-thioproline methyl ester hydrochloride in place of L-proline methyl ester hydrochloride.

EXAMPLE 4

N-[(2-Oxo-1-pyrrolidinyl)acetyl]-L-prolyl-L-prolinal (Compound 4)

A) N-[(2-Oxo-1-pyrrolidinyl)acetyl]-L-prolyl-L-prolinol

N-[(2-Oxo-1-pyrrolidinyl)acetyl]-L-prolyl-L-proline methyl ester (Compound 1) (2.56 g) as obtained in Example 1 was dissolved in a mixture of THF (30 ml) and ethanol (6 ml), to which was added a THF solution of 2 M lithium borohydride (7.3 ml) under ice-cooling. After 3 hours' stirring at room temperature, a 50% acetic acid-methanol solution was added to adjust the pH of the mixture to 6. The residue obtained by concentration was purified by silica gel column chromatography (chloroform-methanol) to give 2.02 g of N-[(2-oxo-1-pyrrolidinyl)acetyl]-L-prolyl-L-prolinol.

B) N-[(2-Oxo-1-pyrrolidinyl)acetyl]-L-prolyl-L-prolinal

To a solution of N-[(2-oxo-1-pyrrolidinyl)acetyl]-L-prolyl-L-prolinol (965 mg) in DMSO (5 ml) were added triethylamine (2.5 ml) and sulfur trioxide pyridine complex (1.89 g) under ice-cooling, and the mixture was stirred at a temperature of 10°-15° C. for 1 hour. The reaction mixture was concentrated at room temperature, and the residue was purified by silica gel column chromatography (chloroform-methanol) to give 663 mg of N-[(2-oxo-1-pyrrolidinyl)acetyl]-L-prolyl-L-prolinal.

EXAMPLES 5 TO 7

By following the procedure of Example 4, the following Compounds 5 to 7 were obtained.

EXAMPLE 5

N-[(2-Oxo-1-pyrrolidinyl)acetyl]-L-prolyl-L-thioprolinal (Compound 5)

The procedure of Example 4 was followed using Compound 2 in place of Compound 1.

EXAMPLE 6

N-[(2-Oxo-1-pyrrolidinyl)acetyl]-L-thioprolyl-L-prolinal (Compound 6)

The procedure of Example 1 was followed using L-thioproline methyl ester in place of L-proline methyl ester in Example 1-A) to give N-[(2-oxo-1-pyrrolidinyl)acetyl]-L-thioprolyl-L-proline methyl ester, which was subjected to the procedure of Example 4.

EXAMPLE 7

N-[(2-Oxo-1-pyrrolidinyl)acetyl]-L-thioprolyl-L-thioprolinal (Compound 7)

The procedure of Example 4 was followed using Compound 3 in place of Compound 1.

EXAMPLE 8

3-{N-[(2-Oxo-1-pyrrolidinyl)acetyl]-L-prolyl}thiazolidine (Compound 8)

N-[(2-Oxo-1-pyrrolidinyl)acetyl]-L-proline as prepared in Example 1-B) (623 mg) was suspended in a mixture of methylene chloride (3 ml) and DMF (5 ml), to which were added HOBt (530 mg) and thiazolidine (0.21 ml). The mixture was cooled to −25° C. and DCC (588 mg) was added thereto. The mixture was stirred at a temperature of −25°-0° C. for 3 hours and at room temperature for 12 hours. The precipitated dicyclohexylurea was filtered off, and the filtrate was concentrated. The residue was purified by silica gel column chromatography (chloroform-methanol) to give 468 mg of 3-{N-[(2-oxo-1-pyrrolidinyl)acetyl]-L-prolyl}thiazolidine.

EXAMPLE 9

3-{N-[(2-Oxo-1-pyrrolidinyl)acetyl]-L-thioprolyl}thiazolidine (Compound 9)

The procedure of Example 8 was followed using N-[(2-oxo-1-pyrrolidinyl)acetyl]-L-thioproline in place of N-[(2-oxo-1-pyrrolidinyl)acetyl]-L-proline to give the title Compound 9.

EXAMPLE 10

N-[(4-Oxo-4-(2-oxo-1-pyrrolidinyl)butanoyl]-L-prolinal (Compound 10)

A) 4-Oxo-4-(2-oxo-1-pyrrolidinyl)butyric acid

A solution of 2-oxopyrrolidine (5.00 g) in THF (60 ml) was cooled to −50° C., and a 1.55 M n-BuLi/THF solution (38 ml) was dropwise added thereto. After 0.5 hour's stirring at −30° C., succinic anhydride (6.00 g) was added dropwise, followed by stirring at a temperature of −30°-−20° C. for 0.5 hour. The reaction mixture was poured into ice water and adjusted to pH 4 with 1N hydrochloric acid, and extracted with n-butanol. The organic layer was washed with saturated brine and concentrated to give 9.42 g of 4-oxo-4-(2-oxo-1-pyrrolidinyl)butyric acid.

B)
N-[4-Oxo-4-(2-oxo-1-pyrrolidinyl)butanoyl]-L-prolinol

A solution of 4-oxo-4-(2-oxo-1-pyrrolidinyl)butyric acid (5.02 g), L-prolinol (2.74 g) and HOBt (3.72 g) in DMF (50 ml) was cooled to −25° C. and DCC (5.64 g) was added thereto. After 3 hours' stirring at a temperature of −25°-0° C., the mixture was stirred at room temperature for 15 hours. The precipitated dicyclohexylurea was filtered off, and the filtrate was concentrated. The residue was dissolved in chloroform and washed with 1N hydrochloric acid, a saturated aqueous solution of sodium bicarbonate and saturated brine in sequence. The organic layer was dried over magnesium sulfate, followed by concentration. The residue was purified by silica gel column chromatography (chloroform-methanol) to give 3.41 g of N-[(4-oxo-4-(2-oxo-1-pyrrolidinyl)butanoyl]-L-prolinol.

C)
N-[(4-Oxo-4-(2-oxo-1-pyrrolidinyl)butanoyl]-L-prolinal

N-[(4-Oxo-4-(2-oxo-1-pyrrolidinyl)butanoyl]-L-prolinol (105 mg) was dissolved in a mixed solvent of benzene (0.25 ml), DMSO (0.79 ml) and triethylamine (0.25 ml), and sulfur trioxide pyridine complex (285 mg) was added thereto under ice-cooling. After 0.5 hour's stirring at a temperature of 10°-15° C., the reaction mixture was poured into ice water, and extracted with chloroform. The organic layer was washed with a saturated aqueous solution of sodium bicarbonate and saturated brine in sequence. The organic layer was dried over magnesium sulfate, followed by concentration. The residue was purified by PLC (chloroform:methanol=49:1) using silica gel to give 65 mg of N-[(4-oxo-4-(2-oxo-pyrrolidinyl)butanoyl]-L-prolinal.

EXAMPLE 11

N-{4-Oxo-4-[3-(2-oxo-1-pyrrolidinyl)propylamino]butanoyl}-L-prolinal (Compound 11)

A)
4-Oxo-4-[3-(2-oxo-1-pyrrolidinyl)propylamino]butyric acid methyl ester

To a solution of 1-(3-aminopropyl)-2-oxopyrrolidine (570 mg) in methylene chloride (10 ml) were added triethylamine (0.67 ml) and 3-carbomethoxy propionylchloride (600 mg) in sequence under ice-cooling and the mixture was stirred for 0.5 hour. After 3.5 hours' stirring at room temperature, the reaction mixture was poured into ice water and extracted with chloroform. The organic layer was washed with 1N hydrochloric acid, a saturated aqueous solution of sodium bicarbonate and saturated brine in sequence, and dried over magnesium sulfate, followed by concentration. The residue was purified by silica gel column chromatography (chloroform-methanol) to give 902 mg of 4-oxo-4-[3-(2-oxo-1-pyrrolidinyl)propylamino]butyric acid methyl ester.

B)
4-Oxo-4-[3-(2-oxo-1-pyrrolidinyl)propylamino]butyric acid

To a solution of 4-oxo-4-[3-(2-oxo-1-pyrrolidinyl)propylamino]butyric acid methyl ester (900 mg) in methanol (10 ml) was added 2N sodium hydroxide (3 ml) under ice-cooling and the mixture was stirred at room temperature for 4 hours. The reaction mixture was concentrated, and the residue was dissolved in water and washed with ether. The aqueous layer was adjusted to pH 5 with 1N hydrochloric acid, and concentrated to dryness. Chloroform was added to the residue and the insoluble materials were filtered off. The filtrate was concentrated to give 850 mg of 4-oxo-4-[3-(2-oxo-1-pyrrolidinyl)propylamino]butyric acid.

C)
N-{4-Oxo-4-[3-(2-oxo-1-pyrrolidinyl)propylamino]butanoyl}-L-prolinol

To a solution of 4-oxo-4-[3-(2-oxo-1-pyrrolidinyl)propylamino]butyric acid (255 mg) and L-prolinol (118 mg) in DMF (5 ml) were added HOBt (157 mg) and DCC (249 mg) at −25° C. and the mixture was stirred at a temperature of −25°-0° C. for 3 hours. After 15 hours' stirring at room temperature, the precipitated dicyclohexylurea was filtered off, and the filtrate was concentrated. The residue was treated in the same manner as in Example 10-B) to give 189 mg of N-{4-oxo-4-[3-(2-oxo-1-pyrrolidinyl)propylamino]butanoyl}-L-prolinol.

D)
N-{4-Oxo-4-[3-(2-oxo-1-pyrrolidinyl)propylamino]-butanoyl}-L-prolinal

N-{4-Oxo-4-[3-(2-oxo-1-pyrrolidinyl)propylamino]-butanoyl}-L-prolinol (85 mg) was dissolved in a mixed solvent of benzene (0.18 ml), DMSO (0.5 ml) and triethylamine (0.18 ml), and sulfur trioxide pyridine complex (200 mg) was added thereto under ice-cooling. After 1 hour's stirring at a temperature of 10°-15° C., the reaction mixture was treated in the same manner as in Example 10-C) to give 55 mg of N-{4-oxo-4-[3-(2-oxo-1-pyrrolidinyl)propylamino]butanoyl}-L-prolinal.

EXAMPLE 12

(2S)-1-(N-Benzyloxycarbonyl-L-prolyl)-2-pyrrolidinecarboxaldehyde oxime (Compound 12)

To a solution of known Z-L-prolyl-L-prolinal (110 mg) in DMF (3 ml) were added hydroxylamine hydrochloride (30 mg) and pyridine (40 μl), and the mixture was stirred at 70° C. for 2 hours. The reaction mixture was concentrated under reduced pressure, and the residue was dissolved in chloroform, followed by washing with saturated brine. The organic layer was dried over magnesium sulfate and concentrated under reduced pressure. The residue was purified by PLC using silica gel (chloroform: methanol=95:5) to give 92 mg of (2S)-1-(N-benzyloxycarbonyl-L-prolyl)-2-pyrrolidinecarboxaldehyde oxime.

EXAMPLES 13 and 14

The procedure of Example 12 was followed with the use of Z-L-prolyl-L-thioprolinal and Z-L-thioprolyl-L-thioprolinal having L-thioproline as a residue in place of L-proline to give the following Compounds 13 and 14, respectively.

EXAMPLE 13

(4R)-3-(N-Benzyloxycarbonyl-L-prolyl)-4-thiazolidinecarboxaldehyde oxime (Compound 13)

EXAMPLE 14

(4R)-3-(N-Benzyloxycarbonyl-L-thioprolyl)-4-thiazolidinecarboxaldehyde oxime (Compound 14)

EXAMPLE 15

(2S)-1-(N-Benzyloxycarbonyl-L-prolyl)-2-pyrrolidinecarboxaldehyde O-acetyloxime (Compound 15)

To a solution of Z-L-prolyl-L-prolinal (110 mg) in DMF (3 ml) were added hydroxylamine hydrochloride (30 mg) and pyridine (40 μl), and the mixture was stirred at 70° C. for 2 hours to give (2S)-1-(N-benzyloxycarbonyl-L-prolyl)-2-pyrrolidinecarboxaldehyde oxime (Compound 12). The reaction mixture was concentrated under reduced pressure. To a solution of the residue in methylene chloride (3 ml) were added pyridine (34 μl) and acetic anhydride (40 μl) and the mixture was stirred at room temperature for 3.5 hours. The reaction mixture was poured into ice water, adjusted to pH 8 with 20% sodium carbonate and extracted with chloroform. The organic layer was washed with saturated sodium hydrogen carbonate and saturated brine in sequence, dried over magnesium sulfate, and concentrated under reduced pressure. The residue was purified by PLC using silica gel (chloroform: acetone=95:5) to give 68 mg of (2S)-1-(N-benzyloxycarbonyl-L-prolyl-2-pyrrolidinecarboxaldehyde O-acetyloxime.

EXAMPLES 16 and 17

The procedure of Example 15 was followed with the use of Z-L-prolyl-L-thioprolinal and Z-L-thioprolyl-L-thioprolinal having L-thioproline as a residue in place of L-proline to give the following Compounds 16 and 17.

EXAMPLE 16

(4R)-3-(N-Benzyloxycarbonyl-L-prolyl)-4-thiazolidinecarboxaldehyde O-acetyloxime (Compound 16)

EXAMPLE 17

(4R)-3-(N-Benzyloxycarbonyl-L-thioprolyl)-4-thiazolidinecarboxaldehyde O-acetyloxime (Compound 17)

EXAMPLE 18

(2S)-1-(N-Benzyloxycarbonyl-L-prolyl)-2-pyrrolidinecarboxaldehyde O-benzyloxime (Compound 18)

To a solution of Z-L-prolyl-L-prolinal (110 mg) in DMF (3 ml) were added O-benzylhydroxylamine hydrochloride (70 mg) and pyridine (40 μl), and the mixture was stirred at 70° C. for 2.5 hours. The reaction mixture was concentrated under reduced pressure. The residue was dissolved in chloroform, and washed with 1N hydrochloric acid, saturated sodium hydrogen carbonate and saturated brine in sequence. The organic layer was dried over magnesium sulfate, and concentrated under reduced pressure. The residue was purified by PLC using silica gel (chloroform: acetone=95:5) to give 87 mg of (2S)-1-(N-benzyloxycarbonyl-L-prolyl)-2-pyrrolidinecarboxaldehyde O-benzyloxime.

EXAMPLE 19

(2S)-1-(N-Benzyloxycarbonyl-L-prolyl)-2-cyanopyrrolidine (Compound 19)

To a solution of Z-L-prolyl-L-prolinal (2.75 g) in DMF (25 ml) were added hydroxylamine hydrochloride (0.67 g) and pyridine (0.78 ml), and the mixture was stirred at 70° C. for 2 hours to give (2S)-1-(N-benzyloxycarbonyl-L-prolyl)-2-pyrrolidinecarboxaldehyde oxime (Compound 12). Selenium dioxide (1.06 g) was added thereto, and the mixture was stirred at 70° C. for 3 hours. The residual selenium dioxide was filtered with suction, and the filtrate was concentrated under reduced pressure. The residue was dissolved in chloroform, and washed with 1N hydrochloric acid, saturated sodium hydrogen carbonate and saturated brine in sequence. The organic layer was dried over magnesium sulfate, and concentrated under reduced pressure. The residue was purified by silica gel column chromatography (hexane-ethyl acetate) to give 2.17 g of (2S)-1-(N-benzyloxycarbonyl-L-prolyl)-2-cyanopyrrolidine.

EXAMPLE 20

(4R)-3-(N-Benzyloxycarbonyl-L-thioprolyl)-4-cyanothiazolidine (Compound 20)

The procedure of Example 19 was followed using Z-L-thioprolyl-L-thioprolinal to give the title Compound 20.

EXAMPLE 21

(2S)-1-[4-Oxo-4-(4-chlorobenzylamino)butanoyl]-2-pyrrolidinecarboxaldehyde O-acetyloxime (Compound 21)

To a solution of N-[4-oxo-4-(4-chlorobenzylamino)-butanoyl]-L-prolinal (304 mg) in DMF (2.5 ml) were added hydroxylamine hydrochloride (75 mg) and pyridine (90 μl), and the mixture was stirred at 70° C. for 2 hours. To a solution of crude (2S)-1-[4-oxo-4-(4-chlorobenzylamino)butanoyl]-2-pyrrolidinecarboxaldehyde oxime as obtained by subjecting the reaction mixture to concentration under reduced pressure, in methylene chloride (4 ml) were added pyridine (0.16 ml) and acetic anhydride (0.19 ml), and the mixture was stirred at room temperature for 5 hours. The reaction mixture was treated in the same manner as in Example 15 to give 249 mg of (2S)-1-[4-oxo-4-(4-chlorobenzylamino)-butanoyl]-2-pyrrolidinecarboxaldehyde O-acetyloxime.

EXAMPLE 22

(2S)-1-[4-Oxo-4-(4-chlorobenzylamino)butanoyl]-2-cyanopyrrolidine (Compound 22)

As in Example 19, N-[4-oxo-4-(4-chlorobenzylamino)butanoyl]-L-prolinal (304 mg) was converted to the corresponding carboxaldehyde oxime, and thereafter reacted with selenium dioxide to give 253 mg of (2S)-1-[4-oxo-4-(4-chlorobenzylamino)butanoyl]-2-cyanopyrrolidine.

EXAMPLE 23

(4R)-3-{N-[(2-Oxo-1-pyrrolidinyl)acetyl]-L-prolyl}-4-thiazolidinecarboxaldehyde O-acetyloxime (Compound 23)

As in Example 15, N-[(2-oxo-1-pyrrolidinyl)acetyl]-L-prolyl-L-thioprolinal (Compound 5) was converted to the corresponding carboxaldehyde oxime, and thereafter subjected to acetylation to give (4R)-3-{N-[(2-oxo-1-pyrrolidinyl)acetyl]-L-prolyl}-4-thiazolidinecarboxaldehyde O-acetyloxime.

EXAMPLE 24

(4R)-3-{N-[(2-Oxo-1-pyrrolidinyl)acetyl]-L-prolyl}-4-cyanothiazolidine (Compound 24)

The title compound was obtained by subjecting N-[(2-oxo-1-pyrrolidinyl)acetyl]-L-prolyl-L-thioprolinal (Compound 5) to the procedure of Example 19.

The physiochemical properties of the Compounds 1 to 24 are as shown in Table 1.

TABLE 1

| Comp. No. | Substituent Q | Y | R | Properties Melting Point | EI—MS (m/z) | $^1H$ NMR (CDCl$_3$, δ value) |
|---|---|---|---|---|---|---|
| 1 | (structure) | CH$_2$ | COOCH$_3$ | colorless needles 156.2~157.3° C. | 351(M$^+$), 253, 195, 126, 98 | 1.9~2.3(10H, m), 2.41(2H, m), 3.39(1H, ddd, J=8.3, 8.3, 6.7Hz), 3.5~3.9(5H, m), 3.71(3H, s), 3.82(1H, d, J=16.3Hz), 4.34(1H, d, J=16.3Hz), 4.55(1H, dd, J=8.5, 4.0Hz), 4.69(1H, dd, J=7.9, 3.9Hz) |
| 2 | (structure) | S | COOCH$_3$ | colorless oily substance | 369(M$^+$), 310(M$^+$—COOCH$_3$), 271, 195, 146, 126, 98 | 1.9~2.3(6H, m), 2.42(2H, m), 3.2~3.7(6H, m), 3.72(3H, s), 3.87(1H, d, J=16.3Hz), 4.29(1H, d, J=16.3Hz), 4.57(1H, d, J=7.5Hz), 4.71(1H, dd, J=7.6, 3.6Hz), 4.91(1H, d, J=7.5Hz), 5.14(1H, dd, J=6.9, 3.1Hz) |
| 3 | (structure) | S | COOCH$_3$ | white foamy substance | 387(M$^+$), 301, 289, 261, 201, 186, 146, 126, 98, 86 | 2.09(2H, m), 2.43(2H, m), 3.2~3.6(6H, m), 3.76(3H, s), 4.09(1H, d, J=16.0Hz), 4.24(1H, d, J=16.0Hz), 4.58(1H, d, J=8.8Hz), 4.59(1H, d, J=7.5Hz), 4.74(1H, d, J=8.8Hz), 4.96(1H, d, J=7.5Hz), 5.06(1H, t, J=7.1Hz), 5.15(1H, dd, J=6.7, 3.1Hz) |
| 4 | (structure) | CH$_2$ | CHO | colorless oily substance | 321(M$^+$), 293(MH$^+$—CHO), 223, 195, 126, 98 | 1.8~2.3(10H, m), 2.42(2H, m), 3.3~4.7(10H, m), 9.50(1H, s) |
| 5 | (structure) | S | CHO | colorless oily substance | 339(M$^+$), 311(MH$^+$—CHO), 283, 195, 126, 98 | 1.8~2.3(6H, m), 2.42(2H, m), 3.0~5.0(12H, m), 9.48(1H, s) |
| 6 | (structure) | CH$_2$ | CHO | colorless oily substance | 339(M$^+$), 310(M$^+$—CHO), 241, 213, 186, 153, 126, 98 | 1.8~2.2(6H, m), 2.42(2H, m), 3.1~3.6(6H, m), 3.85(1H, m), 4.0~4.7(4H, m), 4.99(1H, m), 9.53(1H, m) |
| 7 | (structure) | S | CHO | colorless oily substance | 357(M$^+$), 241, 231, 186, 171, 126, 98 | 2.08(2H, quintet, J=7.6Hz), 2.43(2H, t, J=7.6Hz), 3.1~3.6(6H, m), 4.0~5.2(8H, m), 9.49(1H, d, J=2.1Hz) |

TABLE 1-continued

| Comp. No. | Substituent Q | Y | R | Properties Melting Point | EI—MS (m/z) | ¹H NMR (CDCl₃, δ value) |
|---|---|---|---|---|---|---|
| 8 | (structure: pyrrolidinone with thiolane) | S | H | colorless needles 162~163.5° C. | 311(M⁺), 283, 213, 195, 126, 98 | 1.9~2.3(6H, m), 2.42(2H, m), 2.99(1H, m), 3.12(1H, m), 3.42(1H, m), 3.55~3.75(4H, m), 3.84&4.11(total 1H, m), 3.87&3.88(total 1H, d each, J=16.3Hz), 4.31& 4.32(total 1H, d each, J=16.3Hz), 4.50&4.55(total 1H, d each, J=8.1, 11.1Hz), 4.56&4.79(total 1H, d each, J=11.1, 8.1Hz), 4.68(1H, m) |
| 9 | (structure: pyrrolidinone with thiolane) | S | H | colorless needles 156.2~157.9° C. | 329(M⁺), 203, 186, 143, 126, 98, 88 | 2.08(2H, quintet, J=7.6Hz), 2.44(2H, t, J=7.6Hz), 3.0~3.6(6H, m), 3.7~4.2(2H, m), 4.07(1H, d, J=16.1Hz), 4.27 (1H, d, J=16.1Hz), 4.51&4.56(total 1H, d each, J=8.2, 9.9Hz), 4.60&4.83(total 1H, d each, J=9.9, 8.2Hz), 4.61(1H, d, J=8.8Hz), 4.74(1H, d, J=8.8Hz), 5.05(1H, dd, J=1.49, 7.4Hz) |
| 10 | (structure: pyrrolidinone with butanoyl) | CH₂ | CHO | colorless oily substance | 266(M⁺), 237(M⁺—CHO), 168, 140, 112 | 1.9~2.1(6H, m), 2.59(2H, t, J=8.1Hz), 2.69(2H, t, J=6.1Hz), 3.28(2H, m), 3.67(2H, m), 3.80(2H, t, J=7.2Hz), 4.40(1H, d, J=2.3Hz) |
| 11 | (structure: N-H amide with butanoyl pyrrolidine) | CH₂ | CHO | colorless oily substance | 323(M⁺), 295(MH⁺—CHO), 225, 182, 126, 112, 98 | 1.68(2H, quintet, J=6.4Hz), 1.8~2.1(6H, m), 2.40 (2H, t, J=8.2Hz), 2.57(2H, t, J=8.2Hz), 2.70(2H, m), 3.1~3.7(8H, m), 4.40(1H, m), 6.94(1H, m), 9.48(1H, d, J=2.2Hz) |
| 12 | (structure: benzyl carbamate with pyrrolidinone) | CH₂ | CH=N—OH | colorless oily substance | 345(M⁺), 204, 91 | 1.7~2.3(8H, m), 3.3~3.9(4H, m), 4.1~4.6&4.81 (total 2H, m), 4.9~5.2(2H, m), 6.56, 6.68, 7.47&7.57 (total 2H, m), 7.38(5H, m), d each, J=3.8, 7.4, 3.8, 7.4Hz), 7.35(5H, m), 7.8~8.0&8.4~8.8(total 1H, broad) |
| 13 | (structure: benzyl carbamate with thiolane pyrrolidine) | S | CH=N—OH | white foamy substance | 363(M⁺), 346(M⁺—OH), 292, 239, 204, 131, 91 | 1.8~2.3(4H, m), 2.9~3.7(4H, m), 4.3~5.2(6H, m), 6.73, 6.90, 7.61&7.78(total 1H, m each, J=3.8, 7.4, 3.8, 7.4Hz), 8.1~8.4(1H, broad) |
| 14 | (structure: benzyl carbamate with thiolane pyrrolidine) | S | CH=N—OH | white foamy substance | 381(M⁺), 364(M⁺—OH), 310, 91 | 2.9~3.4(4H, m), 4.4~5.2(8H, m), 7.48(5H, m), 7.42, 7.50&7.74(total 1H, m each), 8.1~8.4 (1H, broad) |

TABLE 1-continued

| Comp. No. | Substituent Q | Y | R | Properties Melting Point | EI—MS (m/z) | $^1$H NMR (CDCl$_3$, δ value) |
|---|---|---|---|---|---|---|
| 15 | benzyl-O-C(=O)-N (6-membered ring) | CH$_2$ | CH=N—OAc | colorless oily substance | 387(M$^+$), 232, 204, 91 | 1.8~2.3(8H, m), 2.10, 2.11, 2.12&2.14(total 3H, s each), 3.3~3.9(4H, m), 4.3~4.7&4.91(total 2H, m each), 4.9~5.3(2H, m), 6.61, 7.68, 7.76&7.92 (total 1H, d each, J=8.3, 3.9, 3.7, 7.4Hz), 7.34(5H, m) |
| 16 | benzyl-O-C(=O)-N (6-membered ring) | S | CH=N—OAc | colorless oily substance | 405(M$^+$), 346(M$^+$—OAc), 292, 270, 232, 204, 91 | 1.8~2.3(4H, m), 2.14&2.17(total 3H, s each), 2.9~3.7(4H, m), 4.4~5.2(6H, m), 7.36(5H, m), 7.63, 7.79 &7.89(total 1H, d each, J=8.0, 4.0, 7.7Hz) |
| 17 | benzyl-O-C(=O)-N (S in ring) | S | CH=N—OAc | white foamy substance | 423(M$^+$), 310, 288, 228, 168, 113, 91, 86 | 2.13(3H, br, s), 2.9~3.4(4H, m), 4.4~5.2(8H, m), 7.35(5H, m), 7.38, 7.61&7.71(total 1H, m each) |
| 18 | benzyl-O-C(=O)-N (6-membered ring) | CH$_2$ | CH=N—O—CH$_2$—phenyl | colorless oily substance | 435(M$^+$), 232, 204, 91 | 1.7~2.3(8H, m), 3.3~3.8(4H, m), 4.2~4.9(2H, m), 5.0~5.2(4H, m), 6.50, 6.55, 7.45&7.64(total 1H, d each, J=8.3, 3.9, 3.8, 7.2Hz), 7.30(5H, m) |
| 19 | benzyl-O-C(=O)-N (6-membered ring) | CH$_2$ | CN | colorless needles 134~135° C. | 327(M$^+$), 232, 204, 91 | 1.7~2.3(8H, m), 3.4~3.9(4H, m), 4.35, 4.49&4.87 (total 2H, m each), 4.90&5.06(total 1H, d each, J=11.8, 12.4Hz), 5.15&5.16(total 1H, d each, J=11.8, 12.4Hz), 7.33(5H, m) |
| 20 | benzyl-O-C(=O)-N (S in ring) | S | CN | colorless oily substance | 363(M$^+$), 310, 228, 195, 168, 113, 91 | 2.9~3.4(4H, m), 4.3~5.4(8H, m), 7.36(5H, m) |

TABLE 1-continued

| Comp. No. | Substituent Q | Y | R | Properties Melting Point | EI—MS (m/z) | $^1$H NMR (CDCl$_3$, δ value) |
|---|---|---|---|---|---|---|
| 21 | 4-Cl-C$_6$H$_4$-CH$_2$-N(H)-C(=O)-CH$_2$CH$_2$CH$_2$- | CH$_2$ | CH=N—OAc | colorless oily substance | 381(M$^+$ + 2), 379(M$^+$), 239, 224, 179, 142, 140, 127, 125 | 1.8~2.3(4H, m), 2.11, 2.12, 2.15&2.16(total 3H, each s), 2.57(2H, m), 2.63(2H, m), 3.51(2H, m), 4.36 (2H, m), 4.72(1H, m), 6.87(1H, broad), 7.20(2H, d, J=8.8Hz), 7.27(2H, d, J=8.8Hz), 7.62&7.68(total 1H, d each, J=4.8Hz) |
| 22 | 4-Cl-C$_6$H$_4$-CH$_2$-N(H)-C(=O)-CH$_2$CH$_2$CH$_2$- | CH$_2$ | CN | colorless oily substance | 321(M$^+$ + 2), 319(M$^+$), 224, 194, 179, 142, 140, 127, 125 | 2.05~2.35(4H, m), 2.5~2.8(4H, m), 3.50(1H, m), 3.65(1H, m), 4.36(1H, dd, J=16.1, 5.7Hz), 4.41(1H, dd, J=16.1, 5.7Hz), 4.61(1H, d, J=5.7Hz), 6.62(1H, broad), 7.21(2H, d, J=8.3Hz), 7.28(2H, d, J=8.3Hz) |
| 23 | pyrrolidinone-CH$_2$- | S | CH=N—OAc | colorless oily substance | 396(M$^+$), 336(M$^+$—AcOH), 283, 195, 126, 98 | 1.9~2.3(6H, m), 2.13, 2.14&2.16(total 3H, s each), 2.43(2H, m), 3.1~3.7(6H, m), 3.85, 3.94, 4.09, 4.17, 4.28&4.33(total 2H, d each, J=16.3Hz), 4.5~5.0 (3H, m), 5.18, 5.38&5.62(total 1H, m each), 7.67, 7.76&7.78(total 1H, d each, J=3.7, 4.6, 7.1Hz) |
| 24 | pyrrolidinone-CH$_2$- | S | CN | white foamy substance | 336(M$^+$), 309(M$^+$—CN), 283, 210, 195, 126, 98 | 1.9~2.3(6H, m), 2.43(2H, m), 3.2~3.7(6H, m), 3.89(1H, d, J=16.3Hz), 4.27(1H, d, J=16.3Hz), 4.57(1H, d, J=7.9Hz), 4.60(1H, m), 4.93(1H, d, J=7.9Hz), 5.30(1H, dd, J=5.8, 2.7Hz) |

The amino acid derivatives of the present invention represented by the formula (I) mentioned above were examined for the in vitro prolyl endopeptidase-inhibitory activity and specificity in inhibitory activities against various endopeptidases.

EXPERIMENT EXAMPLE 1

Prolyl Endopeptidase-Inhibitory Activity

A mixture of a 0.1M potassium sodium phosphate buffer (pH 7.0) (2675 μl), a solution of the compounds of the present invention in a 0.1M potassium sodium phosphate buffer (pH 7.0) (100 μl) and a solution of prolyl endopeptidase extracted from rat brain in a 25 mM sodium phosphate buffer (100 μl) [123 unit/1, pH 6.8, containing 1 mM dithiothreitol and 0.5 mM EDTA, prepared by the method described in J. Neurochem., 35, 527 (1980)] was preincubated at 30° C. for 30 minutes. Thereto was added a 0.2 mM solution of 7-(N-succinyl-glycyl-prolyl)-4-methylcoumarinamide (Peptide Institute, INC.) in a 0.1M potassium sodium phosphate buffer (pH 7.0) (125 μl), and the mixture was incubated at 30° C. for 1 hour. The reaction mixture was immersed in ice (0° C.) to terminate the reaction, and the fluorescence ($a_1$) was determined ten minutes later (excitation at 370 nm and emission at 440 nm). Concurrently, there were conducted the experiment wherein, in the above system, the prolyl endopeptidase solution was substituted for a 25 mM sodium phosphate buffer (pH 6.8, containing 1 mM dithiothreitol and 0.5 mM EDTA) and the experiment wherein the solution of the compounds of the present invention was also substituted for a 0.1M potassium sodium phosphate buffer (pH 7.0). Each fluorescence ($a_2$ and $a_3$) was also determined respectively [See *Tanpakushitsu Kakusan Koso*, 29, 127 (1984)]. The prolyl endopeptidase-inhibition rate was calculated by the following formula, and $IC_{50}$, a concentration of a compound producing 50% inhibition, was estimated by semilogarithmic graph paper.

$$\text{Inhibition rate (\%)} = \left(1 - \frac{a_1 - a_2}{a_3 - a_2}\right) \times 100$$

The results are summarized in Table 2.

As is evident from the experiment results, the compounds of the present invention exhibit superior inhibitory activities against prolyl endopeptidase.

TABLE 2

| Compound No. | $IC_{50}$ (M) |
|---|---|
| 4 | $4.0 \times 10^{-10}$ |
| 5 | $3.0 \times 10^{-9}$ |
| 6 | $1.5 \times 10^{-9}$ |
| 7 | $5.0 \times 10^{-9}$ |

TABLE 2-continued

| Compound No. | $IC_{50}$ (M) |
|---|---|
| 8 | $2.0 \times 10^{-7}$ |
| 9 | $1.5 \times 10^{-7}$ |
| 10 | $7.0 \times 10^{-8}$ |
| 11 | $2.5 \times 10^{-8}$ |
| 12 | $4.5 \times 10^{-7}$ |
| 15 | $4.5 \times 10^{-9}$ |
| 16 | $1.0 \times 10^{-7}$ |
| 17 | $3.1 \times 10^{-7}$ |
| 18 | $4.0 \times 10^{-8}$ |
| 19 | $3.5 \times 10^{-10}$ |
| 20 | $3.2 \times 10^{-9}$ |
| 21 | $4.0 \times 10^{-8}$ |
| 22 | $1.0 \times 10^{-8}$ |
| 23 | $6.4 \times 10^{-7}$ |
| 24 | $3.4 \times 10^{-8}$ |

EXPERIMENT EXAMPLE 2

Inhibitory Activity Against Various Proteases

The compounds of the present invention were examined for specificity in inhibitory activities against various proteases. As a result, it was found that the compounds of the present invention specifically inhibited only prolyl endopeptidase, as shown in the following Table 3.

TABLE 3

| Compound No. | Concentration of the compound (M) | Inhibition rate (%) | | | | | |
|---|---|---|---|---|---|---|---|
| | | prolyl endo-peptidase | trypsin | chymotrypsin | leucine amino-peptidase | elastase | cathepsin B |
| 4 | $1 \times 10^{-8}$ | 100 | 0 | 0 | 0 | 0 | 0 |
| 8 | $1 \times 10^{-5}$ | 96 | 0 | 0 | 0 | 0 | 0 |
| 9 | $1 \times 10^{-5}$ | 97 | 0 | 0 | 0 | 0 | 0 |
| 11 | $1 \times 10^{-6}$ | 97 | 0 | 0 | 0 | 0 | 0 |
| 12 | $1 \times 10^{-5}$ | 100 | 0 | 0 | 0 | 0 | 0 |
| 15 | $1 \times 10^{-6}$ | 100 | 0 | 0 | 0 | 0 | 0 |
| 18 | $1 \times 10^{-5}$ | 100 | 0 | 0 | 0 | 0 | 0 |
| 19 | $1 \times 10^{-8}$ | 100 | 0 | 0 | 0 | 0 | 0 |
| 21 | $1 \times 10^{-6}$ | 100 | 10 | 0 | 0 | 0 | 0 |
| 22 | $1 \times 10^{-6}$ | 100 | 0 | 0 | 0 | 0 | 0 |

The methods for the measurement of inhibitory activities against various proteases and the method for calculating the inhibition rate are as follows.

Determination of Trypsin-Inhibitory Activity

In the present invention, a 50 mM Tris-HCl buffer (pH 8.0) was employed as a buffer for measurement.

To a mixture of the above-mentioned buffer (850 μl), a solution of the compounds of the present invention in the same buffer (50 μl) and a 0.02 μM solution of trypsin (derived from bovine pancreas, Sigma) in the same buffer (50 μl) was added a 200 μM solution of 7-(prolyl-phenylaranyl-arginyl)-4-methylcoumarinamide (Peptide Institute, Inc.) in the same buffer (50 μl), and the mixture was incubated at 30° C. for 1 hour. The reaction mixture was immersed in ice (0° C.) to terminate the reaction, and the fluorescence ($b_1$) was determined 1 hour later (excitation at 370 nm and emission at 440 nm). Concurrently, there were conducted the experiment wherein, in the system above, the trypsin solution was substituted for a buffer alone, and the experiment wherein the solution of the compounds of the present invention was also substituted for a buffer above. Each fluorescence ($b_2$ and $b_3$) was also determined respectively.

Determination of Chymotrypsin-Inhibitory Activity

Similarly, by following the procedure mentioned above, but employing a 50 mM Tris-HCl buffer (pH 8.0) as a buffer for measurement, a 0.2 μM solution of chymotrypsin (derived from bovine pancrease, Sigma) in the same buffer as an enzyme solution and a 200 μM solution of 7-(N-succinyl-leucyl-leucyl-valyl-tyrosyl)-4-methylcoumarinamide (Peptide Institute, Inc.) in the same buffer as a substrate solution. Each fluorescence ($c_1$, $c_2$ and $c_3$) was also determined, respectively.

Determination of Leucine Amminopeptidase-Inhibitory Activity

Similarly, by following the procedure mentioned above, but employing a 50 mM Tris-HCl buffer (pH 8.0) as a buffer for measurement, a 0.2 μM solution of leucine aminopeptidase (derived from swine kidney, Sigma) in the same buffer as an enzyme solution and a 200 μM solution of 7-(leucyl-4-methylcoumarinamide (Peptide Institute, Inc.) in the same buffer as a substrate solution. Each fluorescence ($d_1$, $d_2$ and $d_3$) was also determined, respectively.

Determination of Elastase-Inhibitory Activity

Similarly, by following the procedure mentioned above, but employing a 1 mM Tris-HCl buffer (pH 8.5) as a buffer for measurement, a 0.2 μM solution of elastase (derived from swine pancreas, Sigma) in the same buffer as an enzyme solution and a 200 μM solution of 7-(N-succinyl-aranyl-prolyl-aranyl)-4-methylcoumarinamide (Peptide Institute, Inc.) in the same buffer as a substrate solution. Each fluorescence ($e_1$, $e_2$ and $e_3$) was also determined, respectively.

Determination of Cathepsin B-Inhibitory Activity

Similarly, by following the procedure mentioned above, but employing a 100 mM sodium phosphate buffer (pH 6.0; containing 1.33 mM EDTA $Na_2$) as a buffer for measurement, a 0.02 μM solution of cathepsin B (derived from bovine spleen, Sigma) in the same buffer as an enzyme solution and a 200 μM solution of 7-(N-benzyloxycarbonyl-phenylaranyl-arginyl)-4-methylcoumarinamide (Peptide Institute, Inc.) in the same buffer as a substrate solution. Each fluorescence ($f_1$, $f_2$ and $f_3$) was also determined, respectively.

Using the fluorescence $x_1$, $x_2$ and $x_3$ measured in the above-mentioned manner, the inhibitory rate against various proteases was calculated by the following formula where x stands for b, c, d, e or f:

$$\text{Inhibition rate (\%)} = \left(1 - \frac{x_1 - x_2}{x_3 - x_2}\right) \times 100.$$

INDUSTRIAL APPLICABILITY OF THE INVENTION

As is evident from the results of the in vitro experiments shown in Table 2 mentioned above, the novel amino acid derivatives of the formula (I) of the present invention exhibit very strong prolyl endopeptidase-inhibitory activities, while exhibiting no inhibitory activity against proteases such as trypsin, chymotrypsin, leucine aminopeptidase, elastase and cathepsin B, as shown in Table 3. Thus, the compounds of the present invention can be put to use as an agent which specifically inhibits decomposition and inactivation of intracerebral hormones containing proline residues, neurotransmitters and peptides which are considered to be concerned with learning and memory process, such as TRH, substance P, neurotensin, vasopressin, or the like.

Based on such characteristic properties, the compounds of the present invention are expected to contribute to the improvement of the symptoms of various diseases concerned with hormones and neurotransmitters, and in addition, can be used for the prevention and/or treatment of dementia and amnesia as agents therefor which act directly on the central symptoms of dementia.

We claim:

1. An amino acid derivative selected from the group consisting of N-[(2-oxo-1-pyrrolidinyl)acetyl]-L-prolyl-L-proline methyl ester, N-[(2-oxo-1-pyrrolidinyl)acetyl]-L-prolyl-L-thioproline methyl ester, N-[(2-oxo-1-pyrrolidinyl)acetyl]-L-thioprolyl-L-thioproline methyl ester, N-[(2-oxo-1-pyrrolidinyl)acetyl]-L-prolyl-L-prolinal, N-[(2-oxo-1-pyrrolidinyl)acetyl]-L-prolyl-L-thioprolinal, N-[(2-oxo-1-pyrrolidinyl)acetyl]-L-thioprolyl-L-prolinal, N-[(2-oxo-1-pyrrolidinyl)acetyl]-L-thioprolyl-L-thioprolinal, 3-{N-[(2-oxo-1-pyrrolidinyl)acetyl]-L-prolyl}thiazolidine, 3-{N-[(2-oxo-1-pyrrolidinyl)acetyl]-L-thioprolyl}thiazolidine, N-[(4-oxo-4-(2-oxo-1-pyrrolidinyl)butanoyl]-L-prolinal, N-{4-oxo-4-[3-(2-oxo-1-pyrrolidinyl)propylamino]butanoyl}-L-prolinal, (2S)-1-(N-benzyloxycarbonyl-L-prolyl)-2-pyrrolidinecarboxaldehyde oxime, (4R)-3-(N-benzyloxycarbonyl-L-prolyl)-4-thiazolidinecarboxaldehyde oxime, (4R)-3-(N-benzyloxycarbonyl-L-thioprolyl)-4-thiazolidinecarboxaldehyde oxime, (2S)-1-(N-benzyloxycarbonyl-L-prolyl)-2-pyrrolidinecarboxaldehyde O-acetyloxime, (4R)-3-(N-benzyloxycarbonyl-L-prolyl)-4-thiazolidinecarboxaldehyde O-acetyloxime, (4R)-3-(N-benzyloxycarbonyl-L-thioprolyl)-4-thiazolidinecarboxaldehyde O-acetyloxime, (2S)-1-(N-benzyloxycarbonyl-L-prolyl)-2-pyrrolidinecarboxaldehyde O-benzyloxime, (2S)-1-(N-benzyloxycarbonyl-L-prolyl)-2-cyanopyrolidine, (4R)-3-(N-benzyloxycarbonyl-L-thioprolyl)-4-cyanothiazolidine, (2S)-1-[4-oxo-4-(4-chlorobenzylamino)butanoyl]-2-pyrrolidinecarboxaldehyde O-acetyloxime, (2S)-1-[4-oxo-4-(4-chlorobenzylamino)butanoyl]-2-cyanopyrolidine, (4R)-3-{N-[(2-oxo-1-pyrrolidinyl)acetyl]-L-prolyl}-4-thiazolidinecarboxaldehyde O-acetyloxime and (4R)-3-{N-[(2-oxo-1-pyrrolidinyl)acetyl]-L-prolyl}-4-cyanothiazolidine.

* * * * *